United States Patent
Zhang

(10) Patent No.: US 11,690,909 B2
(45) Date of Patent: *Jul. 4, 2023

(54) COMPOSITION FOR TREATING AND/OR PREVENTING HEPATITIS B VIRUS INFECTION AND THE USE THEREOF

(71) Applicant: Yisheng Biopharma (Singapore) Pte Ltd, Singapore (SG)

(72) Inventor: Yi Zhang, Beijing (CN)

(73) Assignee: Yisheng Biopharma (Singapore) Pte Ltd, Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 17/408,811

(22) Filed: Aug. 23, 2021

(65) Prior Publication Data

US 2022/0211840 A1    Jul. 7, 2022

Related U.S. Application Data

(63) Continuation of application No. 16/630,972, filed as application No. PCT/SG2018/050391 on Aug. 1, 2018, now Pat. No. 11,135,286.

(30) Foreign Application Priority Data

Aug. 10, 2017    (SG) .......................... 10201706540X

(51) Int. Cl.
| | | |
|---|---|---|
| *A61K 39/29* | (2006.01) | |
| *A61P 31/20* | (2006.01) | |
| *A61K 9/00* | (2006.01) | |
| *A61K 31/7084* | (2006.01) | |
| *A61K 39/00* | (2006.01) | |

(52) U.S. Cl.
CPC .......... *A61K 39/292* (2013.01); *A61K 9/0019* (2013.01); *A61K 31/7084* (2013.01); *A61P 31/20* (2018.01); *A61K 2039/545* (2013.01)

(58) Field of Classification Search
CPC ................ A61K 39/292; A61K 9/0019; A61K 31/7084; A61K 2039/545; A61K 2039/55505; A61K 2039/55511; A61K 2039/55561; A61K 39/39; A61P 31/20; A61P 37/04
See application file for complete search history.

(56) References Cited

U.S. PATENT DOCUMENTS

| | | |
|---|---|---|
| 9,738,646 B2 | 8/2017 | Brown et al. |
| 2005/0025780 A1 | 2/2005 | Rubido et al. |
| 2007/0160632 A1 | 7/2007 | Haixiang |
| 2015/0086610 A1 | 3/2015 | Davis et al. |
| 2020/0038506 A1 | 2/2020 | Sepp-Lorenzino et al. |
| 2020/0163878 A1 | 5/2020 | Baumhof et al. |

FOREIGN PATENT DOCUMENTS

| | | |
|---|---|---|
| CN | 101501055 | 5/2016 |
| TW | I660948 | 9/2016 |
| WO | WO 2007081287 | 7/2007 |

OTHER PUBLICATIONS

Akbar et al., (2013) "HBsAg, HBcAg, and combined HBsAg/HBcAg-based therapeutic vaccines in treating chronic hepatitis B virus infection", Hepatobiliary & Pancreatic Diseases International, (12)4:363-369.

Chuai et al., (2013) "Poly(I:C)/alum mixed adjuvant priming enhances HBV subunit vaccine-induced immunity in mice when combied with recombinant adenoviral-based HBV vaccine boosting." PLOS One., 8(1):e54126, 9 pages.

Mahtab et al., (2013) "760 A Phase ITT Clinical Trial With A Nasal Vaccine Containing Both HBsAg And HBcAg In Patients With Chronic Hepatitis B", Journal of Hepatology, (58):S309.

Shen et al., (2007) "PIKA as an adjuvant enhances specific humoral and cellular immune responses following the vaccination of mice with HBsAg plus PIKA", Cellular & Molecular Immunology,. 4(2):113-120.

Xiao-Yu et al., (2011) "Stability of PIKA Recombinant Hepatitis B Vaccine (Hansenula polymorpha)", Chinese Journal Of Biologicals, (24)6:693-694.

*Primary Examiner* — Rachel B Gill
(74) *Attorney, Agent, or Firm* — Bozicevic, Field & Francis LLP; Shweta Chandra

(57) ABSTRACT

A composition for treating and/or preventing Hepatitis B virus infection and Hepatitis B virus infection mediated diseases and the method thereof are provided. In some embodiments, the composition includes a polyriboinosinic acid-polyribocytidylic acid (PIC), at least one antibiotic or polyamide compound, at least one positive ion, and Hepatitis B virus surface antigen. In some embodiments, the composition includes PIC, at least one antibiotic or polyamide compound, at least one positive ion, Hepatitis B virus surface antigen and Hepatitis B virus core antigen. The present disclosure also relates to a method of treating and/or preventing Hepatitis B virus infection, particularly for treating chronic HBV infection.

21 Claims, 4 Drawing Sheets

COMPOSITION FOR TREATING AND/OR PREVENTING HEPATITIS B VIRUS INFECTION AND THE USE THEREOF

RELATED APPLICATION

This application claims priority to Singapore application NO. 10201706540X, filed on Aug. 10, 2017. The entire teachings of the above application are incorporated herein by reference.

TECHNICAL FIELD

This application relates to a composition for treating and/or preventing Hepatitis B virus infection and Hepatitis B virus infection mediated diseases. More particularly, this application relates to compositions, including a polyriboinosinic acid-polyribocytidylic acid (PIC), at least one antibiotic or polyamide compound, at least one positive ion, Hepatitis B virus surface antigen, and/or Hepatitis B virus core antigen. This application also relates to a method of treating and/or preventing Hepatitis B virus infection or Hepatitis B virus infection mediated diseases.

BACKGROUND

Hepatitis B virus (HBV) infection is an important global health problem. Nearly 2 billion of people are hepatitis B carriers, and about 400 million of them are suffering from persistent infection (European Association for the Study of the Liver, EASL Clinical Practice Guidelines: management of chronic hepatitis B virus infection. J. Hepatol. 2012. 57 (1):167-185). Liver cirrhosis, hepatic insufficiency, or liver cancer develop in 15%-40% of patients with chronic infection (Lok A S, McMahon B J, Chronic hepatitis B: update 2009. Hepatology. 2009. 50 (3):661-662). It is estimated that 600,000 people die from consequences of the chronic infection every year, such as liver cirrhosis and liver cancer (Lok A S et al., Chronic Hepatitis B. Hepatology. 2007. 45:507-539; World Health Organization, Hepatitis B (Fact sheet No. 204). 2013; National Institutes of H. National Institutes of Health consensus development conference statement: Management of Hepatitis B. Ann Intern Med. 2009. 150:104-110).

Currently, 10 μg or 20 μg Hepatitis B virus surface antigen (HBsAg) is used in a preventive hepatitis B vaccine. However, 40 μg HBsAg may be administered to patients who receive hemodialysis treatment or pre-transplantation patients (Mahoney F J., Update on Diagnosis, Management, and Prevention of Hepatitis B Virus Infection, Clin. Microbiol. Rev. 1999, 12:351-366; Bock M et al., Hepatitis B vaccination in haemodialysis patients: A randomized clinical trial. Nephrology 2009; 14:267-272; Somi M H et al., Improving hepatitis B vaccine efficacy in end-stage renal diseases patients and role of adjuvants. ISRN Gastroenterol. 2012; 2012:960413; Bauer T and Jilg W., Hepatitis B surface antigen-specific T and B cell memory in individuals who had lost protective antibodies after hepatitis B vaccination, Vaccine 2006; 24:572-577). Under clinical conditions, it is safe to administer a vaccine including 60 μg, 80 μs, or 90 μs HBsAg.

Hepatitis B virus core antigen (HBcAg), which is located on the internal component of the HBV particle, is one indication of the HBV infection or HBV infection mediated diseases. United States patent application No. 20170049817 disclosed preparation of a composition against HBV using a modified HBcAg. The entire content of the United States patent application No. 20170049817 is incorporated herein by reference.

Furthermore, some patients are susceptible to HBV, and show resistance to standard immunization protocols. When receiving hemodialysis treatments, patients with end-stage renal diseases show higher prevalence rate and more adverse prognosis than normal people. However, after vaccination with HBV vaccines, patients with uremia or pre-transplantation patients show significantly lower seroconversion rate than that in individuals with immunity. Even though the protective antibodies are generated, peak antibody titers are low and duration of immune responses is also short (Bauer T. and Jilg W., Hepatitis B surface antigen-specific T and B cell memory in individuals who had lost protective antibodies after Hepatitis B vaccination, Vaccine 2006; 24:572-577; Bock M, Barros E and JV Veronese F, Hepatitis B vaccination in haemodialysis patients: A randomized clinical trial, Nephrology 2009; 14, 267-272).

When a vaccine including 40 μg HBsAg (double of generally used dosage) is administered to a dialysis patient, effect of the vaccine is unsatisfactory, and only about 50% to 60% of all vaccinated subjects have developed protective antibodies (Mary S et al., High-Dose Hepatitis B Vaccine in Patients Waiting for Lung Transplantation, Presentation at the Fifth Annual Conference on Vaccine Research, Baltimore, Md., May 7, 2002).

Furthermore, only 5% of adults have developed chronic infection after acutely infected with HBV. If a subject is infected in perinatal period, the subject is more likely to get chronic infection. After first acute infection, 25%-30% of children below 5 years old have developed chronic infection, and 90% of infants born by HBeAg positive mothers have risk for acquiring chronic infection (Mahoney F J, Update on Diagnosis, Management, and Prevention of Hepatitis B Virus Infection, Clin. Microbiol. Rev. 1999; 12:351-366). Also, immunosuppressed patients after an acute infection (for example, HIV infection) are prone to develop chronic HBV infection (Mehta N et al., Impaired generation of hepatitis B virus-specific memory B cells in HIV infected individuals following vaccination. Vaccine. 2010. 7; 28(21): 3672-8).

U. S. Food and Drug Administration (US FDA) has approved following drugs as alternatives of chronic HBV infection treatments: polyethyleneglycol (PEG) modified IFN-α, and nucleoside or nucleotide analogues (for example, Lamivudine). Chronic HBV infection treatments and these drugs are used to arrest disease development, which means long-term administration of antivirus drugs or PEG modified IFN-α is inevitable.

However, currently, an antivirus treatment often represents a failure. About 30% of the patients have achieved the goals of the treatment, and only 10% of the patients are deemed to be cured. A long-term antivirus treatment is more likely to generate resistance to virus, and IFN-α can produce significant side effects (Nebbia G et al., Hepatitis B infection: current concepts and future challenges. QJM. 2012. 105(2):109-13). Therefore, a treatment with adequate therapeutic effects to chronic infection is needed.

Multi-specific antivirus CD4$^+$ and CD8$^+$ T cell responses are observed in patients recovered from acute infection. These responses are stronger than those in chronic patients, and virus-specific T cell responses in chronic patients are weak and instant (Webster, G. J et al., Longitudinal analysis of CD8$^+$ T cells specific for structural and nonstructural Hepatitis B virus proteins in patients with chronic Hepatitis B: implications for immunotherapy. J Virol. 2004; 78:5707-

5719; Urbani, S et al., Acute phase HBV-specific T cell responses associated with HBV persistence after HBV/HCV co-infection. Hepatology. 2005; 41:826-831).

Therefore, it is a potentially promising strategy to develop therapeutic vaccines by effectively activating $CD4^+$ and $CD8^+$ T cell immune responses (Sobao Y et al., J Hepatol 2002; 36:105-15; Sette A D et al., The Journal of Immunology 2001; 166: 1389-1397; Chang, J. J et al., J Virol 2005; 79:3038-3051; Guidotti L G et al., Science 1999; 284:825-9; Webster, G. J et al., Hepatology 2000; 32:1117-1124; Wieland, S. F. & Chisari, F. V. J Virol 2005; 79:9369-9380; Webster, G. J et al., J Virol 2004; 78:5707-719; Urbani, S et al., Hepatology 2005; 41:826-31; Maini, M. K et al., J Exp Med 2000; 191:1269-1280).

It is reported that high-titer $CD4^+$ and $CD8^+$ T cell immune responses are capable of removing virus in acute HBV infection (Mary S et al., High-Dose Hepatitis B Vaccine in Patients Waiting for Lung Transplantation, Presentation at the Fifth Annual Conference on Vaccine Research, Baltimore, Md., May 7, 2002; Rehermann B et al., Nature Reviews Immunology 2005; 5:215-229; Bertoletti A et al., Journal of Hepatology 2003; 39:115-124; Bertoletti A et al., Journal of General Virology 2006; 87:1439-1449; Guidotti L G et al., Ann Rev Immunol 2001; 19:65-91; Ferrari C et al., J Immunol 1990; 145:3442-9; Penna A et al., J Clin Invest 1996; 98:1185-94; Penna A et al., Hepatology 1997; 25:1022-7; Rehermann B et al., J Exp Med 1995; 181:1047-58; Jung M et al., Virology 1999; 261:165-72).

According observations from preclinical studies, some methods are capable of decreasing HBV DNA load. For example, one method is performing short-term antivirus wash by Lamivudine before vaccination. For another example, some methods include eliciting T cell mediated immune responses to HBsAg vaccines (Bertoletti A et al., Curr Opin Immunol 2000; 12:403-8; Chisari F V. American Journal of Pathology 2000; 156:1117-1132; Kakimi K et al., J Exp Med 2000; 192:921-30; Kakimi K et al., J Immunol 2001; 167:6701-5; Thimme R et al., J Virol 2003; 77:68-76; Pol S et al., Lancet. 1994; 344:342; Mancini M et al., Proc Natl Acad Sci USA. 1996; 93:12496-12501).

Alum adjuvant is generally used to activate antibody mediated immunity, and helps build effective prevention against HBV infection. However alum adjuvant is not able to develop effective T cell mediated immune responses.

Polyriboinosinic acid-polyribocytidylic acid (PIC, also referring to Poly I:C) is proved to be a strong immunomodulator in animal tests, but not in human tests, possibly due to fast degradation by human serum nucleases.

A stabilized PIC, also referring to PIKA (a composition including PIC, one or more antibiotics or polyamide compounds, one or more positive ions, and any other substance for preparing the PIKA), is capable of being dissolved by solutions (PH: 6.0-8.0). PIKA is capable of enhancing production of neutralizing antibodies, and inducing T cell mediated immunity (Li L et al., Zhong Guo Mian Yi Xue Za Zhi 2006; 22:983-986). According to the present disclosure, PIC, antibiotics and positive ions may be those disclosed in WO2006/131023. The disclosure of WO2006/131023 is incorporated herein by reference.

United States patent application publication NO. 20090136538A1 discloses that commercially available Hepatitis B vaccine is a liquid suspension consisting of purified HBsAg absorbed onto aluminum hydroxide adjuvant. Hepatitis B vaccine is a heat-stable vaccine, but a 50% loss of potency of the vaccine has been reported to be observed after 9 months at 20° C. to 26° C., after 1 month at 36° C. to 40° C., and after 3 days at 45° C. So a stable Hepatitis B vaccine is needed to allow wider immunization coverage and to boost safety of the immunization, especially in some developing countries or regions. The entire disclosure of United States patent publication NO. 20090136538A1 is incorporated herein by reference.

SUMMARY

A composition for treating and/or preventing Hepatitis B virus infection or HBV infection mediated diseases, and a method of its use are provided. In some embodiments, the composition includes PIC, at least one antibiotic or polyamide compound, at least one positive ion, and HBsAg. In some embodiments, the composition includes PIC, at least one antibiotic or polyamide compound, at least one positive ion, HBsAg and HBcAg.

In some embodiments, concentration of PIC in the composition ranges from 250 µg/unit dose to 6000 µg/unit dose. In some embodiments, ratio of HBsAg to PIC ranges from 1:50 to 1:5. In some embodiments, ratio of the HBcAg to PIC ranges from 1:50 to 1:5.

In some embodiments, the unit dose represented by volume ranges from 0.1 ml to 250.0 ml.

According to one aspect of the present disclosure, the composition is capable of eliciting protective antibody production, and/or $CD4^+$ and $CD8^+$ T cell mediated immune responses. The composition is capable of preventing HBV infection, alleviating HBV infection, arresting HBV infection development, and/or removing HBV.

According to one aspect of the present disclosure, the composition is capable of being administered to a HBV uninfected subject, a chronic HBV subject, and an acute HBV subject, and eliciting or enhancing immune responses against HBV.

According to one aspect of the present disclosure, the composition is administered to a subject at a frequency. In some embodiments, the frequency may include once every two months, twice every two months, three times every two months, four times every two months, five times every two months, once every month, twice every month, once every three weeks, twice every three weeks, twice every two weeks, once every two weeks and once every week.

According to another aspect of the present disclosure, the present disclosure provides a kit. The kit includes at least one container. In some embodiments, the container includes the composition, or at least one component of the composition.

BRIEF DESCRIPTION OF THE DRAWINGS

The present disclosure is further described in terms of exemplary embodiments. Some of these exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
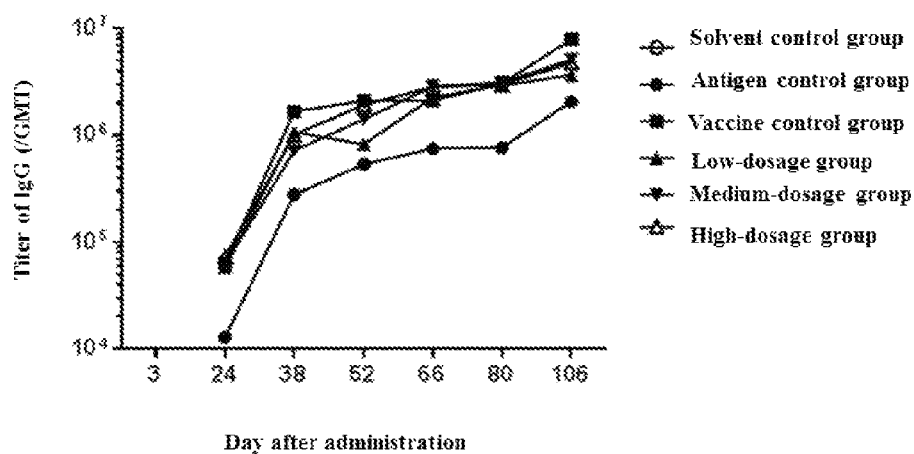
FIG. 1 illustrates production of anti-HBsAg IgG of mice after administration according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. Various modifications to the disclosed embodiments are also apparent to those skilled in the art, and general principles defined herein may be applied to other embodiments and applications without departing from the spirit and scope of the present disclosure.

It will be understood that unless defined otherwise, all technical and scientific terms used herein have the same meaning as commonly understood by those skilled in the art.

It will be understood that the singular forms "a", "and", and "the" include plural referents unless the context clearly dictates otherwise. As used herein, the term "and/or" includes any and all combinations of one or more of the associated listed items. It will be further understood that the terms "include", and/or "comprise", when used in this disclosure, specify the presence of elements, steps, operations, and/or components, but not exclude the presence or addition of one or more other elements, steps, operations, and/or components thereof.

It should be noted that unless indicated otherwise, term "treating", or "treatment", means alleviating HBV infection, arresting disease development, and/or removing HBV by administering the composition and eliciting or enhancing immune responses. Unless indicated otherwise, term "preventing", or "prevention", means developing effective defense against virus invasion by administering the composition and eliciting or enhancing immune responses.

The present disclosure provides a composition for treating and/or preventing HBV infection. In some embodiments of the present disclosure, the composition includes PIC, at least one antibiotic or polyamide compound, at least one positive ion, and HBsAg. In some embodiments of the present disclosure, the composition may further include HBcAg and/or any other component for implementing the composition.

It should be noted that components of the composition are not limiting. According to some embodiments of the present disclosure, the components of the composition are one or more, usually a combination of specific attributes. The specific attributes may include molecular weight, molecular size, concentration, PH, dissolvability, or any other attributes in accordance with the present disclosure. For example, the composition may include several substances (e.g., sodium bicarbonate) to adjust the PH of the composition.

According to some embodiments of the present disclosure, PIC molecules of the composition are heterogeneous in molecular weight. The term "heterogeneous" used herein means the PIC molecules in the composition have different molecular weights. In some embodiments, the PIC molecules with their molecular weights equal to or greater than 66,000 Daltons (66,000 Daltons equals to 6.4 Svedbergs) may be used in the composition. For example, PIC molecules, of which molecular weights are between 66,000 Daltons and 1,200,000 Daltons (i.e., between 6.4 and 24.0 Svedbergs), may be used in the composition. For another example, the molecular weights of the PIC molecules may be greater than 150,000 Daltons. In some embodiments, molecular weights of the PIC molecules may range from 100,000 Daltons to 200,000 Daltons, from 300,000 Daltons to 4,000,000 Daltons, from 500,000 Daltons to 1,000,000 Daltons, from 1,000,000 Daltons to 1,500,000 Daltons, from 1,500,000 Daltons to 2,000,000 Daltons, from 2,000,000 Daltons to 2,500,000 Daltons, from 2,500,000 Daltons to 3,000,000 Daltons, from 3,000,000 Daltons to 3,500,000 Daltons, from 3,500,000 Daltons to 4,000,000 Daltons, from 4,000,000 Daltons to 4,500,000 Daltons, or from 4,500,000 Daltons to 5,000,000 Daltons.

According to some embodiments of the present disclosure, the antibiotic in the composition may be tobramycin, anthracycline, butyrosin sulfate, gentamicin, hygromycin, amikacin, dibekacin, nebramycin, beta-lactam, neomycin, puromycin, streptomycin, streptozotocin, kanamycin, or the like, or any combination thereof. In some embodiments, the antibiotic may be kanamycin.

According to the present disclosure, concentration of the antibiotic may range from 10 unit/ml to 100,000 unit/ml. In one particular embodiment, the concentration of the antibiotic may range from 100 unit/ml to 10,000 unit/ml. In another particular embodiment, the concentration of the antibiotic may range from 500 unit/ml to 5,000 unit/ml. It should be noted that the concentration may be set according to several attributes (e.g., side-effects of long-term or high-dosage antibiotic use, induction of anti-antibiotic microorganism, etc.). In some embodiments, the concentration of the antibiotic (e.g., kanamycin) is not greater than 1000 IU/ml according to preclinical safety and toxicology evaluation.

It should be noted that to those skilled in the art, the antibiotic and the concentration are not limiting. In some embodiments, the antibiotic and the concentration may be set according to characteristics of the subject (e.g., age, antibiotic allergy, etc.) and any other characteristics. For example, for children under 5 years old, the concentration of the antibiotics may decrease. For example, for subjects allergic to ampicillin-like antibiotics, the antibiotic in the composition may be non-ampicillin antibiotic (e.g., kanamycin, etc.)

According to some embodiments of the present disclosure, the positive ion is provided by a salt or complex, including an organic or inorganic salt or complex (e.g., chloride, fluoride, hydroxide, phosphate, sulfate, etc.). For example, the positive ion may be calcium, which may be provided by calcium carbonate, calcium chloride, calcium fluoride, calcium hydroxide, calcium phosphate, or calcium sulfate. Exemplary positive ions may include, but not limited to, calcium, cadmium, lithium, magnesium, cerium, cesium, chromium, cobalt, deuterium, gallium, iodine, iron, and/or zinc. In one particular embodiment, the positive ion may be calcium. According to some embodiments of the present disclosure, concentration of the positive ion may range from 0.01 μmol/unit dose to 10 mmol/unit dose. In one particular embodiment, the concentration of the positive ion ranges from 0.02 μmol/unit dose to 5 mmol/unit dose. In another particular embodiment, the concentration of the positive ion ranges from 0.1 μmol/unit dose to 1 mmol/unit dose. In one more particular embodiments, the concentration of the positive ion ranges from 0.1 μmol/unit dose to 100 μmol/unit dose.

According to some embodiments of the present disclosure, concentration of the PIC may range from 250 μg/unit dose to 6000 μg/unit dose. In some embodiments, the concentration of the PIC may be 250 μg/unit dose, 500 μg/unit dose, 1000 μg/unit dose, 1500 μg/unit dose, 2000 μg/unit dose, 3000 μg/unit dose, 4000 μg/unit dose, 5000 μg/unit dose, or 6000 μg/unit dose. The concentration of the PIC is not limiting. The concentration of the PIC may be any value between 250 μg/unit dose and 6000 μg/unit dose. For example, the concentration of the PIC may range from 500 μg/unit dose to 4000 μg/unit dose, 1000 μg/unit dose to 3000 μg/unit dose, 1000 μg/unit dose to 2500 μg/unit dose.

According to some embodiments of the present disclosure, when the composition is administered to adults, the concentration of the PIC may be 500 μg/unit dose, 1000 μg/unit dose, 1500 μg/unit dose, 2000 μg/unit dose, or any value between 500 μg/unit dose and 2000 μg/unit dose. When the composition is administered to juveniles (e.g., children), the concentration of the PIC may be 250 μg/unit dose, 500 μg/unit dose, 1000 μg/unit dose, 1250 μg/unit dose, or any value between 250 μg/unit dose and 1250 μg/unit dose.

According to some embodiments of the present disclosure, the unit dose may represent weight, volume, or any other characteristic of a particular dose of the composition. For example, the unit dose may represent volume of one individual package (e.g., a tablet) of the composition. The unit dose may represent weight, volume, or any other characteristic of a component of the composition. For example, the unit dose may represent concentration of the PIC or PIKA in one particular dose of the composition. In some embodiments, the unit dose may represent volume of one particular dose of the composition. Merely by way of example, value of the unit dose represented by volume of one individual package may be 0.1 ml, 0.15 ml, 0.2 ml, 0.5 ml, 1.0 ml, 1.5 ml, 2.0 ml, 2.5 ml, 3.0 ml, 4.0 ml, 5.0 ml, 10.0 ml, 20.0 ml, 30.0 ml, 40.0 ml, 50.0 ml, 60.0 ml, 70.0 ml, 80.0 ml, 90.0 ml, 100.0 ml, 150.0 ml, 200.0 ml, 250.0 ml, or any value between 0.1 ml and 250.0 ml. It is understood to those skilled in the art, high or low unit dose may not be convenient for clinical operations. The value of the unit dose may be set according to some attributes including administration methods (e.g., nasal delivery, intravenous injection, oral delivery, etc.), characteristics of subjects (e.g., human, body weight, vaccination history, etc.), characteristics of the composition (e.g., concentration of the PIC, PH of the composition, etc.), and/or any other attribute. For example, when the composition is administered by injection to human subjects or other subjects with similar height or similar weight, value of the unit dose may range from 0.5 ml to 1.0 ml. For another example, when the administration method is nasal delivery, value of the unit dose may range from 0.15 ml to 0.2 ml. More particularly, for another example, when the composition is administered by intravenous injection to human subjects or other subjects with similar size or similar weight, value of the unit dose may range from 30.0 ml to 100.0 ml. It should be noted that although the unit dose used herein represents volume of the composition, it does not mean the composition is limited to a liquid composition. For example, when the composition is in the solid form (e.g., dry powder, freeze-dried powder, etc.) and may be further prepared into a liquid form, the unit dose may represent volume of the composition in the liquid form.

According to some embodiments of the present disclosure, the composition may further include substances to stabilize the composition. Merely by way of example, the substances may include gelatin, saccharose, granulated sugar, lactose, maltose, trehalose, glucose, low molecular dextran, sorbitol, polysorbate 20, mannitol PEG, human blood albumin, recombinant human serum albumin, sodium caprylate, urea, aluminum hydroxide, phenol red, magnesium chloride, potassium chloride, sodium chloride, sodium thiosulphate, potassium dihydrogen, ascorbic acid, trichloromethane, phenol, thiomersal, or the like, or any combination thereof.

According to some embodiments of the present disclosure, the composition may further include a physiologically acceptable buffer. Merely by way of example, the physiologically acceptable buffer may include acetate buffer, trisamine buffer, bicarbonate buffer, carbonate buffer, phosphate buffered saline, or the like, or any combination thereof. PH value of the physiologically acceptable buffer may range from 6.0 to 8.0. In some embodiments, PH value of the physiologically acceptable buffer may be 6.0, 6.5, 6.6, 6.7, 6.8, 6.9, 7.0, 7.1, 7.2, 7.3, 7.4, 7.5, 7.6, 7.7, 7.8, 7.9, 8.0, or any value between 6.0 and 8.0. In some particular embodiments, the physiologically acceptable buffer is phosphate buffered saline (PH: 7.3-7.5).

According to some embodiments of the present disclosure, the composition may be in the form of dry powder, solution (e.g., parenteral solution, aqueous solution, saline solution, suspension, ointment, drop, emulsion, gel, syrup, serous, etc.), tablet, coated tablet, suppository, pill, granule, sugar-coated tablet, capsule, or the like, or any combination thereof. In some embodiments, the composition may be prepared into a parenteral solution. The form of the composition is not limiting. Forms of a composition and their preparation described in the related art (e.g., Stanley A Plotkin et al., Vaccine, 4$^{th}$ edition, W.B. Saunders Company 2003) are within the spirit and scope of the present disclosure.

According to some embodiments of the present disclosure, HBsAg may be produced by organisms including *Hansenula Polymorpha*, Chinese hamster ovary cell (CHO cell), *Pichia pastoris*, insect expression system, or the like, or any combination thereof. The HBsAg with purity greater than 99% may be administered to infants, children over 5 years old, and adults. According to some embodiments of the present disclosure, the HBcAg may be produced by recombinant DNA methods. The HBcAg may be produced by *Escherichia coli, Hansenula Polymorpha, Pichia pastoris, Saccharomyces cerevisiae*, insect expression system, or the like, or any combination thereof.

In some embodiments, weight ratio of HBsAg to the PIC may be 1:50, 1:40, 1:30, 1:25, 1:20, 3:50, 1:15, 1:10, 1:5, or any value between 1:50 and 1:5. In some particular embodiments, the weight ration of HBsAg to the PIC may be 1:25. It should be noted that the weight ratio of HBsAg to the PIC is not limiting. For example, a composition with weight ratio of HBsAg to the PIC near 1:25 (e.g., 10% lower or higher) is capable of providing adequate safety, and eliciting earlier also stronger (i.e., antibodies of higher titer are generated) humoral immune responses and T cell mediated immune responses.

In some embodiments, concentration of the HBsAg in the composition may range from 10 μg/unit dose to 100 μg/unit dose. Merely by way of example, the concentration of the HBsAg in the composition may be 10 μg/unit dose, 15 μg/unit dose, 20 μg/unit dose, 25 μg/unit dose, 30 μg/unit dose, 35 μg/unit dose, 40 μg/unit dose, 50 μg/unit dose, 60 μg/unit dose, 70 μg/unit dose, 80 μg/unit dose, 90 μg/unit dose, 100 μg/unit dose, or any value between 10 μg/unit dose and 100 μg/unit dose. In some embodiments, the concentration of the HBsAg in the composition may be 20 μg/unit dose, 40 μg/unit dose, or 60 μg/unit dose.

In some embodiments, concentration of the HBcAg in the composition may range from 10 μg/unit dose to 100 μg/unit dose. Merely by way of example, the concentration of the HBcAg in the composition may be 10 μg/unit, 15 μg/unit dose, 20 μg/unit dose, 25 μg/unit dose, 30 μg/unit dose, 35 μg/unit dose, 40 μg/unit dose, 50 μg/unit dose, 60 μg/unit dose, 70 μg/unit dose, 80 μg/unit dose, 90 μg/unit dose, 100 μg/unit dose, or any value between 10 μg/unit dose and 100 μg/unit dose. In some embodiments, the concentration of the HBcAg may range from 10 μg/unit dose to 50 μg/unit dose, or from 50 μg/unit dose to 100 μg/unit dose.

According to some embodiments of the present disclosure, the composition may be administered to HBV uninfected subjects, subjects with chronic HBV infection (also referring to "chronic subjects" or "chronic HBV subjects" in the present disclosure), and subjects with acute HBV infection (also referring to "acute subjects" or "acute HBV subjects"). In some embodiments, the composition of the present disclosure is able of eliciting stronger $CD4^+$ T cell and $CD8^+$ T cell immune responses than a combination of antigen and alum adjuvant. For example, the composition of the present disclosure may elicit higher cytokine production (2-30 times) than the combination of antigen and alum adjuvant.

In one particular embodiment, the composition may include 20 μg/unit dose HBsAg, 20 μg/unit dose HBcAg and 500 μg/unit dose PIC. In another particular embodiment, the composition may include 40 μg/unit dose HBsAg, 40 μg/unit dose HBcAg and 1000 μg/unit dose PIC.

According to one aspect of the present disclosure, the composition may be used for treating and/or preventing HBV infection, preferably chronic HBV infection.

According to one aspect of the present disclosure, the composition for treating and/or preventing HBV infection is in the form of dry powder or freeze-dried powder.

According to one aspect of the present disclosure, the composition may be used to manufacture medicines for treating and/or preventing HBV infection. In some embodiments, the medicines may include preventive vaccines, therapeutic vaccines, vaccine preparations, or the like, or any combination thereof. In one particular embodiment, the composition may be used to prepare medicines for treating and/or preventing chronic HBV infection.

According to another aspect of the present disclosure, a method for treating and/or preventing HBV infection is provided. The method may be configured according to characteristics of the composition (e.g., unit dose, PH, etc.), administration methods (e.g., oral delivery, nasal delivery, intravenous injection, etc.), characteristics of subjects (e.g., age, gender, antibiotic allergy, etc.), purpose of use (e.g., treatment or prevention against HBV infection), and/or any other attribute for implementing administration of the composition to the subjects. Merely by way of example, in some embodiments, when the composition is used to treat HBV infection, the method may include administering the composition of a treatment effective amount to the subjects. Similarly, when the composition is used to prevent HBV infection, the method may include administering the composition of a prevention effective amount to the subjects. The term "treatment effective amount" used herein refers to an amount enough to elicit T cell mediated immune responses and alleviate or remove infection. The term "prevention effective amount" used herein refers to an amount enough to elicit protective antibodies against virus infection. For example, as recommended by World Health Organization (WHO), concentration of the protective antibodies may be at least 10 mIU/ml.

In some embodiments, the method may be configured according to characteristics of the composition. The characteristics of the composition may include unit dose, PH of the composition, or the like. For example, the method may include adjusting the PH of the composition to 6.0-8.0 by adding a physiological acceptable buffer into the composition. For another example, the method may include administrating the composition of a certain amount (e.g., an amount smaller, greater, or equal to a unit dose) to subjects according to value of the unit dose.

In some embodiments, the method may be configured according to administration methods. For example, the administration may be systematically or locally. The administration methods may include parenteral injection (e.g., intramuscular injection, intraperitoneal injection, intravenous injection, subcutaneous injection, intradermal delivery, intratumor delivery, peritumoral delivery, etc.), transdermal delivery, and any other way of administration for implementing the method. More particularly, in some embodiments, the administration methods may further include rectal delivery, vagina delivery, nasal delivery, oral delivery, opthamalical delivery, sublingual delivery, and inhalation. It should be noted that the administration methods are not limiting. To those skilled in the art, various modifications and changes are still within the sprite and scope of the present disclosure.

In some embodiments, the method may be configured according to frequency of administration. The frequency of administration may be once every two months, two times every two months, three times every two months, four times every two months, five times every two months, once every month, twice every month, once every three weeks, twice every three weeks, twice every two weeks, once every two weeks, once every week, or any other suitable frequency for implementing the method. For example, when the composition is administered to HBV uninfected subjects, a composition of a prevention effective amount may be administered to the subjects three times every two months, twice every month, or three times every six months. For another example, when the composition is administered to HBV infected subjects, a composition of a treatment effective amount may be administered to the subjects four times every two months, five times every two months, two times every month, once every three weeks, two times every three weeks, or once every week. According to the present disclosure, a month equals to 28, 29, 30, or 31 days, and one week equals to 7 days.

In some particular embodiments, the method may include administrating (e.g., by intramuscular injection) the composition to a subject three times every two months. For example, the method may include following steps:

1) on day 0, administering the composition of a first amount to a subject;

2) from day 25 to day 31, administering the composition of a second amount to the subject;

3) from day 53 to day 59, administering the composition of a third amount to the subject.

The first amount, the second amount, and the third amount may be the same, or different with each other. For example, at least one of the first amount, the second amount and the third amount equals to a treatment effective amount, or a prevention effective amount. For another example, at least one of the first amount, the second amount and the third amount is set according to concentration of HBsAg (e.g., 20 µg/unit dose, 40 µg/unit dose, etc.), concentration of HBcAg (e.g., 10 µg/unit dose, 20 µg/unit dose, 50 µg/unit dose, 100 µg/unit dose, etc.), and/or concentration of PIC (e.g., 500 µg/unit dose, 1000 µg/unit dose). In some embodiments, at least one of the first amount, the second amount and the third amount includes 20 µg/unit dose HBsAg and 500 µg/unit dose PIC. In some embodiments, at least one of the first amount, the second amount, and the third amount includes 40 µg/unit dose HBsAg and 1000 µg/unit dose PIC. In some embodiments, at least one of the first amount, the second amount, and the third amount includes 10 µg/unit dose to 50 µg/unit dose HBcAg. In some embodiments, at least one of the first amount, the second amount, and the third amount includes 50 µg/unit dose to 100 µg/unit dose HBcAg.

According to some embodiments of the present disclosure, a kit for treating and/or preventing HBV infection is provided. The kit may include at least one of one container, one needle, water for injection, a manual, or the like, or any combination thereof. For example, the kit may include three containers. The composition contained in the containers may include the same or different formation and/or amount of the composition. For example, at least one container (e.g., two, or three containers) may include 20 µg/unit dose HBsAg and 500 µg/unit dose PIC. At least one container (e.g., two, or three containers) may include 10 µg/unit dose to 20 µg/unit dose HBcAg. For another example, at least one container (e.g., two, or three containers) may include 40 µg/unit dose HBsAg and 1000 µg/unit dose PIC. At least one container (e.g., two, or three containers) may include 50 µg/unit dose to 100 µg/unit dose HBcAg. In some other embodiments, the composition in one container may be in a liquid form (e.g., suspension, solution, etc.). In some embodiments, the composition in one container may be in a solid form (e.g., dry powder, freeze-dried powder, etc.). The composition in solid form may be prepared into a liquid form (e.g., suspension, solution, etc.), and stored in one or more sterilized containers (e.g., a tube, a bottle, an ampoule, a syringe, etc.) before use.

EXAMPLES

Example 1: Preparation of the Compositions

In some embodiments, the composition includes HBsAg, PIC, kanamycin, and calcium chloride, where ration of the HBsAg to PIC is 1:25. More particularly, the composition includes 40 µg/unit dose HBsAg, 1000 µg/unit dose PIC, 800 IU/unit dose kanamycin, and 0.16 µmol/unit dose $Ca^{2+}$.

In some embodiments, the composition includes HBcAg, HBsAg, PIC, kanamycin, and calcium chloride. The composition includes 40 µg/unit dose HBsAg, 1000 µg/unit dose PIC, 800 IU/unit dose kanamycin, and 0.16 µmol/unit dose $Ca^{2+}$. More particularly, concentration of the HBcAg ranges from 10 µg/unit dose to 50 µg/unit dose.

In some embodiments, the composition includes HBcAg, HBsAg, PIC, kanamycin, and calcium chloride. The composition includes 40 µg/unit dose HBsAg, 1000 µg/unit dose PIC, 800 IU/unit dose kanamycin, and 0.16 µmol/unit dose $Ca^{2+}$. More particularly, concentration of the HBcAg ranges from 50 µg/unit dose to 100 µg/unit dose.

Example 2: Preclinical Toxicology Studies

EXAMPLE 2 illustrates preclinical toxicology studies of the composition and its main components (including PIC, at least one antibiotic or polyamide compound, and at least one positive ion, collectively, "PIKA") according to some embodiments of the present disclosure. As illustrated in Table 1, mice used in EXAMPLE 2 have an average body weight of 0.019 kg, and can tolerate 0.2 ml of the composition which includes 8 µg HBsAg (0.4 mg/kg) and 200 µg PIC (10 mg/kg), or tolerate 0.2 ml of the PIKA which includes 200 µg PIC (10 mg/kg). Dosage of the composition used in the mice is about 1,200 times higher than that recommend dosage used in a human being (20 µg HBsAg (0.0003 mg/kg) and 500 µg PIKA (0.0083 mg/kg)). Recommended maximum dosage used in a human being is double of the recommended minimum dosage, which provides a Margin of Safety (MoS) of 600. According to chronic toxicology studies of rodent rats, values of the MoS are 600 to recommended minimum dosage in human, and 300 to recommended maximum dosage in human, respectively. According to preclinical studies of primates, values of the MoS are 40 to recommended minimum dosage in human, and 20 to recommended maximum dosage in human, respectively.

TABLE 1

| MoS in preclinical toxicology studies | | |
|---|---|---|
| Safety | MoS of PIC or PIKA | MoS of the composition |
| Acute toxicology of rodents | | |
| Recommended minimum dosage in human | 1,200 | 1,200 |
| Recommended maximum dosage in human | 600 | 600 |
| Chronic toxicology of rodents | | |
| Recommended minimum dosage in human | 600 | 600 |
| Recommended maximum dosage in human | 300 | 300 |
| Chronic toxicology of primates | | |
| Recommended minimum dosage in human | 40 | 40 |
| Recommended maximum dosage in human | 20 | 20 |

Considering body weight of an exemplary human subject is 60 kg, MoS is defined as follows: MoS = (dosage used in preclinical studies, mg/kg) ÷ (recommended dosage in human, mg/kg)

Example 3: Preclinical Studies of Immune Responses of Rodents

Methodology

Rodents used in EXAMPLE 3 are BALB/c mice of 6 weeks old, which are divided into 6 groups. Each group includes 18 mice (9 males, with body weight ranging from 17.3 g to 20.7 g; 9 females, with body weight ranging from 19.0 g to 23.7 g). As illustrated in Table 2, the composition and other substances are administered to the mice on day 1, day 8, day 22, day 36, day 50, day 64 and day 78 by tibialis anterior injection.

TABLE 2

Administration schedule

| Group | Group name | BALB/c mice | HBsAg (μg) | PIKA (μg) adjuvant | Alum (μg) | PBS (μl) control |
|---|---|---|---|---|---|---|
| 1 | Solvent control group | 9M, 9F | — | — | — | 250 |
| 2 | Antigen control group | 9M, 9F | 15 | — | — | — |
| 3 | Vaccine control group | 9M, 9F | 3 | — | 80 | — |
| 4 | Low-dosage group | 9M, 9F | 3 | 50 | — | — |
| 5 | Medium-dosage group | 9M, 9F | 9 | 150 | — | — |
| 6 | High-dosage group | 9M, 9F | 15 | 250 | — | — |

On day 3, day 24, day 38, day 52, day 66, day 80, and day 106, blood samples are taken for measurement of titer of anti-HBsAg antibodies, in order to determine humoral immune responses.

On day 38, day 80, and day 106, three males and three females from each group are sacrificed in order to determine T cell mediated immune responses. HBsAg or HBsAg CD8$^+$ peptide is used for in vitro stimulation of spleen cells. Frequency of the spleen cells producing IFN-γ is measured by ELISPOT.

Results

Figure 2:
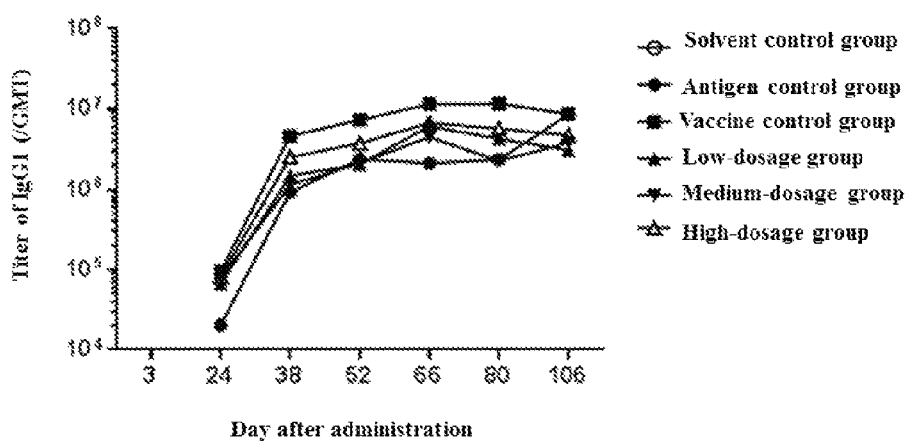
FIG. 2 illustrates production of anti-HBsAg IgG1 of mice after administration according to some embodiments of the present disclosure.
Figure 3:
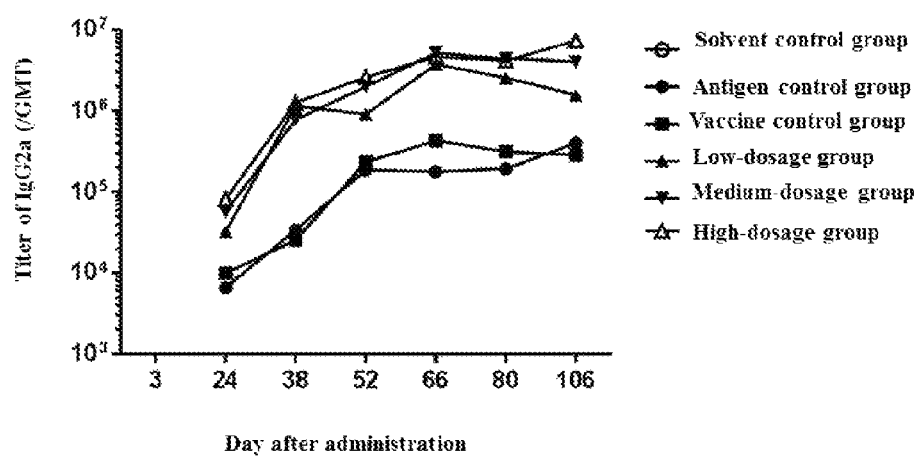
FIG. 3 illustrates production of anti-HBsAg IgG2a of mice after administration according to some embodiments of the present disclosure.

As illustrated in FIG. 1, FIG. 2, and FIG. 3, the composition (including HBsAg and PIKA) elicits stronger humoral immune responses (represented by production of IgG, IgG1, and IgG2a), which indicates PIKA significantly enhances immune responses against HBsAg.

According to FIG. 3, the composition produces strong Th1 type immune response and significantly increases production of IgG2a.

Figure 4:
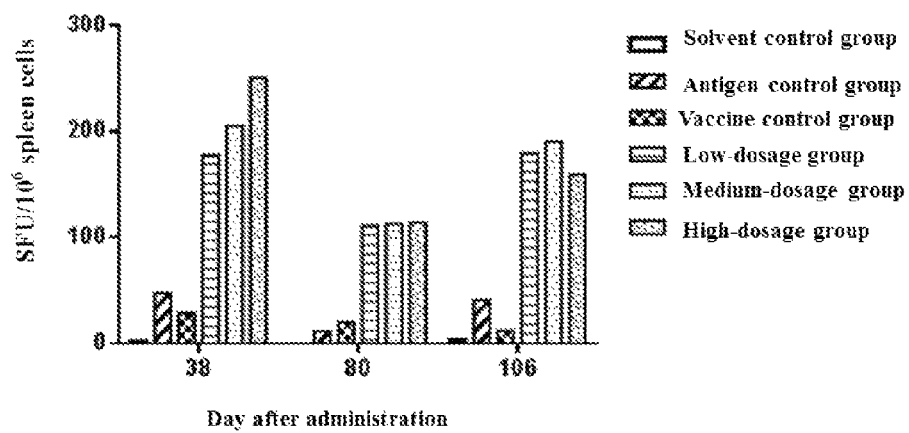
FIG. 4 is a diagram illustrating numbers of IFN-γ spot forming cells in spleen cells of mice after administration according to some embodiments of the present disclosure.

According to FIG. 4, results of the ELISPOT experiments indicate that numbers of the spleen cells producing IFN-γ significantly increase after the in vitro stimulation. The composition (including HBsAg and PIKA) significantly enhances T cell mediated immune responses.

Increasing value of IgG2a titer indicates that main immune responses elicited by the composition belong to Th1 type immune responses. Th1 type immune responses and cellular immune responses are important effects of therapeutic vaccines. The Th1 type immune responses prevent virus infection, and remove infected cells. In addition, increasing number of the spleen cells producing IFN-γ indicates that the composition significantly enhances cellular immune responses.

Example 4: Chronical Toxicology Studies of Primates

Laboratory:

EXAMPLE 4 is conducted at National Center for Safety Evaluation of Drugs, National Institute for the Control of Pharmaceutical and Biological Products, P.R. China.

Methodology

The primates used in EXAMPLE 4 are Rehsus monkeys divided into five groups. Each group includes 8 Rehsus monkeys (4 females and 4 males; 1.6-3.2 years old; 3-3.5 kg). The composition, HBsAg, PIKA or PBS is administered to the primates 5 times (on day 0, day 14, day 28, day 56, and day 84) in three months according to Table 3.

TABLE 3

Grouping and administration schedule

| Group | Animal | HBsAg Dosage (μg) | HBsAg Concentration (mg/kg) | PIKA Dosage (μg) | PIKA Concentration (mg/kg) | Control |
|---|---|---|---|---|---|---|
| 1 | 4M, 4F | — | — | 1,000 | 0.31 | — |
| 2 | 4M, 4F | 40 | 0.012 | — | — | — |
| 3 | 4M, 4F | 40 | 0.012 | 1,000 | 0.31 | — |
| 4 | 4M, 4F | 60 | 0.018 | 1,500 | 0.46 | — |
| 5 | 4M, 4F | — | — | — | — | PBS |

Each group receives 40 μg HBsAg and 1,000 μg PIC (or PIKA), or 60 μg antigen HBsAg and 1,500 μg PIC (or PIKA).

Local (e.g., administration site) and systematic clinical symptoms are observed, and blood samples are taken 5 times from day 2 to day 126. On day 85 (i.e., 24 hours after fifth administration) and day 126, the monkeys are sacrificed. 36 organs of the female monkeys and 32 organs of the male monkeys are used for histological examinations.

Histological Examinations

The histological examinations include:

clinical symptoms, appearance, hair, activity, reaction, respiration, posture, head-shoulder (including eyes, ears, mouth, nose), abdomen, anus, perineum, skin color, muscle tension, trauma, tumor;

symptom related behaviors;

symptoms of administration site;

body weight;

feeding;

body temperature;

hematology: T, APTT, RBC, WBC, HGB, HCT, MCV, MCH, MCHC, PLT, MPV, reticulocytes count %, Neut %, Lymph %, Mono %, Eos %, Baso %;

biochemical tests: AST, ALT, BUN, CHO, GLU, TBIL, CRE, ALP, CK, LDH, TP, ALB, TG, GGT, Ca, P, K$^+$, Na$^+$, Cl$^-$, IgA, IgG, IgM, C3, C4;

urine test;

pathological and histological analysis of the following organs: brain, spine cord, heart, artery, lung (including bronchus), liver, kidneys, spleen, pancreas, stomach, duodenum, jejunum, ileum, colon, rectum, caecum, testis, epididymis, prostate, ovary, uterus, vagina, bladder, pituitary gland, thyroid, parathyroid, submandibular gland, adrenal gland, sciatic nerve, muscles, mesenteric lymph nodes, inguinal lymph nodes, thymus, mammary gland, sternum, administration site;

humoral immune response: antibody titers in serum measured by ELISA.

Results

No local or systematic symptoms are observed. No abnormal changes are observed in hematologic tests and serum biochemical tests. Results of spleen histological test show increased numbers of activated macrophages and mitosis in germinal centers of spleen white pulp. The germinal centers of spleen white pulp are main areas of lymphocyte proliferation, especially main areas of B cell activation after antigen stimulation. PIKA enhances immune responses against antigen, and elicits lymphocyte proliferation. No spleen necrosis or cell death is observed. Therefore, the results indicate histological changes of spleen are not pathological, but physiological; the immune responses are reversible. Abnormal phenomena are not observed in histological results of any other organs.

The antibody titers in serum indicate the primates develop enhanced humoral immune responses after administration of a composition including HBsAg and PIKA. Table 4 illustrates immune response of the primates.

TABLE 4

Antibody titers in serum

| Group | HBsAg (mg/kg) | PIC or PIKA (mg/kg) | Day 0 | Day 21 | Day 43 | Day 85 | Day 100 | Day 126 |
|---|---|---|---|---|---|---|---|---|
| 1 | — | 0.31 | 0 | 0 | 0 | 0 | 0 | 0 |
| 2 | 0.012 | — | 0 | 2 | 6 | 148 | 620 | 253 |
| 3 | 0.012 | 0.31 | 0 | 72 | 444 | 1585 | 4502 | 2379 |
| 4 | 0.018 | 0.46 | 0 | 140 | 602 | 5261 | 11459 | 4912 |
| 5 | PBS | | 0 | 0 | 0 | 0 | 0 | 0 |

Example 5: Clinical Studies of the Composition in Health Human Subjects

Laboratory

Department of Gastroenterology and Hepatology of Singapore General Hospital, Singapore; Clinical Trials & Research Unit of Changi General Hospital, Singapore.

Methodology

Health human subjects are randomly divided into three groups. Two of three groups receive increasing dose of the composition, and the third group receives a commercially available HBV vaccine. The composition and vaccine are administered as an intramuscular injection in the deltoid region of the upper arm.

Composition and Vaccine

Group A (or "half dosage" group): the composition including 20 μg HBsAg and 500 μg PIKA;

Group B (or "full dosage" group): the composition including 40 μg HBsAg and 1000 μg PIKA;

Group C (or "control" group): a vaccine including 20 μg HBsAg and 500 Alum adjuvant (e.g., commercially available vaccine from GSK: ENGERIX™-B)

Administration Schedule

To implement double-blind tests, the subjects receive the composition or the vaccine three times and placebo once in 6 months as illustrated in Table 5.

TABLE 5

Administration schedule

| group | Day 0 | Day 7 | Day 28 | Day 56 | Day 84 | Day 168 | Day 196 |
|---|---|---|---|---|---|---|---|
| A&B | x | | x | x | | o | |
| C | x | | x | | o | | x | x means administration of the composition or the vaccine; o means administration of the placebo.

Results

1. Safety Profile of Dosage

Dosage of the composition and the vaccine used in EXAMPLE 5 is based on the dosage in EXAMPLE 1. Preclinical toxicology studies of the primates and rodents provide main information for safety profile. EXAMPLE 2 evaluates tolerance of the composition, or PIKA only.

Use of commercially available vaccines is also taken into consideration. The commercially available vaccines are generally administered three times in 6 months (10 μg or 20 μg HBsAg). For dialysis subjects and subjects who are about to receive transplantation, a vaccine is administered 4 times (40 μg HBsAg), each of which may be performed in month 0, month 1, month 2, and month 6.

Preclinical immunological studies further valid that the recommended dosages provide adequate immune responses.

According to the results, when the ratio of antigen to PIKA equals to or is near 1:25, the humoral immune responses and T cell mediated immune responses reach adequate balance. To those skilled in the art, increasing the ratio of antigen to PIKA (1:25) may enhance the humoral immune responses.

To apply a high dosage of HBsAg (40 μg) to the clinical studies, the composition includes 1000 μg of PIKA according to the ratio (1:25). According to the results of EXAMPLE 1, the subjects can tolerate 40 μg HBsAg and 1000 μg PIKA. To decrease clinical risks, subjects in the half-dosage group are administrated 20 μg HBsAg and 500 μg PIKA. The safety profile of the half-dosage group indicates the combination of 40 μg HBsAg and 1000 μg PIKA is optimal.

2. Optimized Administration Schedule

By modifying conventional administration schedule (three times in 6 months), the composition is more effective. The present disclosure further provides an accelerated administration schedule to elicit protective anti-virus antibody production. More particularly, the accelerated administration schedule has more frequent of administration than the conventional administration schedule, as a result of which, the accelerated administration schedule may elicit T cell mediated immune responses. In EXAMPLE 5, the administration schedule (three times in 2 months) provides enough time to decrease risk of subjects between two administration intervals, and enough time to observe immune responses.

3. Antibody Titers

Results of the humoral immune responses are based on evaluation of the blood samples of each group collected on day 0, day 56, day 84, and day 196. The blood samples are evaluated to acquire titers of the anti-HBV antibodies. The results show immunogenicity of the composition over the control group (group C, commercial available vaccine ENGERIX™-B). According to Table 6, the results indicate both full-dosage group (Group B) and half-dosage group (Group A), once applied the accelerated administrated schedule, generate stronger and earlier immune responses.

TABLE 6

Numbers and percentages of subjects who obtain titer of 10 mIU/ml

| | | The composition | | | Numbers and percentages of subjects who obtain titer of 10 mIU/ml | | | |
|---|---|---|---|---|---|---|---|---|
| | | HBsAg | PIKA | Alum | | | | |
| Group | N | (μg) | (μg) | (μg) | Day 0 | Day 56 | Day 84 | Day 196 |
| A | 11 | 20 | 500 | — | 0 (0%) | 8 (72.73%) | 10 (90.91%) | 10 (90.91%) |
| B | 10 | 40 | 1000 | — | 0 (0%) | 10 (100%) | 10 (100%) | 10 (100%) |
| C | 11 | 20 | — | 500 | 0 (0%) | 6 (54.55%) | 7 (63.64%) | 9 (81.82%) |

N means number of the subjects in a group

WHO recommends that standard titer of anti-virus antibodies should be 10 mIU/ml to provide protection from HBV infection. According to Table 6, on day 56 (i.e., after the second administration), all subjects in the full-dosage group have obtained the standard titer, while 72.73% of the subjects in the half-dosage group and 54.55% of the subjects in the control group have obtained the standard titer. On day 196, percentages of the subjects having the standard titer in full-dosage group, half-dosage group and control group are 100%, 90.91%, and 81.82%, respectively.

TABLE 7

Numbers and percentages of subjects who obtain titer of 150 mIU/ml

| | | The composition | | | Numbers and percentages of subjects who obtain titer of 150 mIU/ml | | | |
|---|---|---|---|---|---|---|---|---|
| | | HBsAg | PIKA | Alum | | | | |
| Group | N | (μg) | (μg) | (μg) | Day 0 | Day 56 | Day 84 | Day 196 |
| A | 11 | 20 | 500 | | 0 (0%) | 3 (27.27%) | 9 (81.82%) | 10 (90.91%) |
| B | 10 | 40 | 1000 | | 0 (0%) | 4 (40%) | 10 (100%) | 10 (100%) |
| C | 11 | 20 | | 500 | 0 (0%) | 4 (36.36%) | 4 (36.36%) | 5 (45.45%) |

N means total number of the subjects

According to Table 7, subjects in full-dosage group (Group B) and half-dosage group (Group A) acquire stronger humoral immune responses on day 84 and day 196, respectively. On day 84, all subjects in full-dosage group obtain titer of antibodies over 150 mIU/ml; 81.82% of the subjects in half-dosage group, and 36.36% of the subjects in control group, obtain titer of antibodies over 150 mIU/ml. On day 196, percentages of subjects who obtain titer over 150 mIU/ml in full-dosage groups, half-dosage group, and control group are 100%, 90.91%, and 45.45%, respectively.

Figure 5:
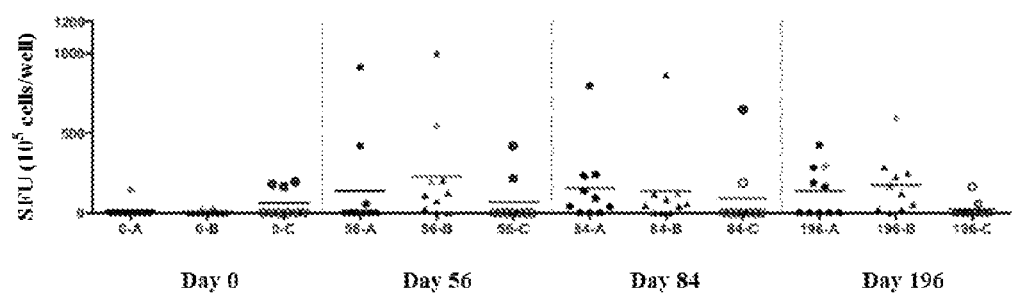
FIG. 5 is a diagram illustrating numbers of IFN-γ spot forming cells in PBMC of health human subjects after administration according to some embodiments of the present disclosure.

The clinical studies further investigate HBV specific T cell mediated immune responses. The HBV specific T cell mediated immune responses are evaluated by Spot Forming Unit (SFU) in each well (including $10^5$ cells). As illustrated in FIG. 5, on day 56, average SFU of the subjects in full-dosage group (Group B) and half-dosage group (Group A) are 230 and 138, respectively, while no SFU is observed in control group (Group C). On day 84, the average SFU of the subjects in full-dosage group and half-dosage group are 134 and 157, respectively, while the average SFU of subjects in control group is 186. On day 196, the average SFU of the subjects in full-dosage group and half-dosage group are similar to those on day 84, while the average SFU of subjects in control group is only 24.

Figure 6:
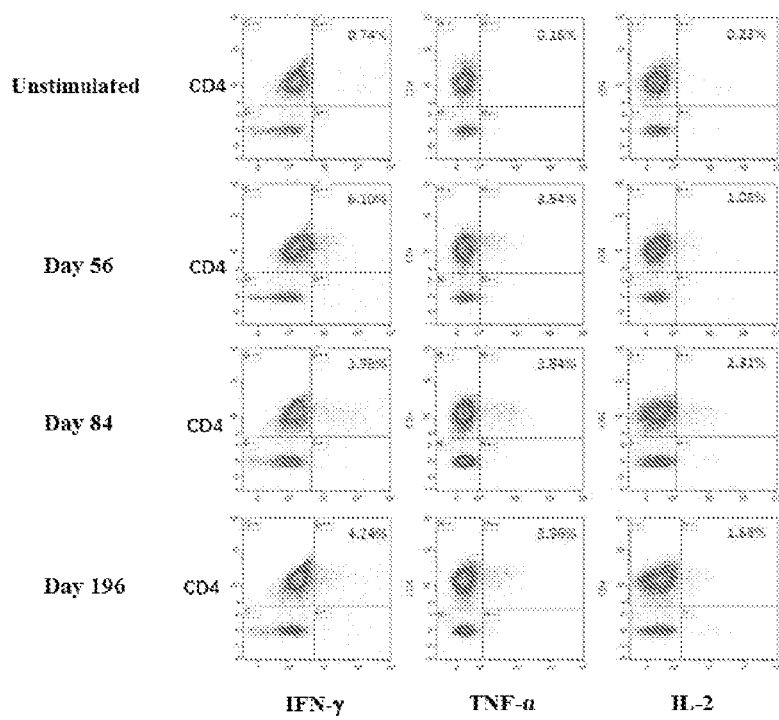
FIG. 6 illustrates a flow cytometry spectrum of one subject in full-dosage group according to some embodiments of the present disclosure.
Figure 7:
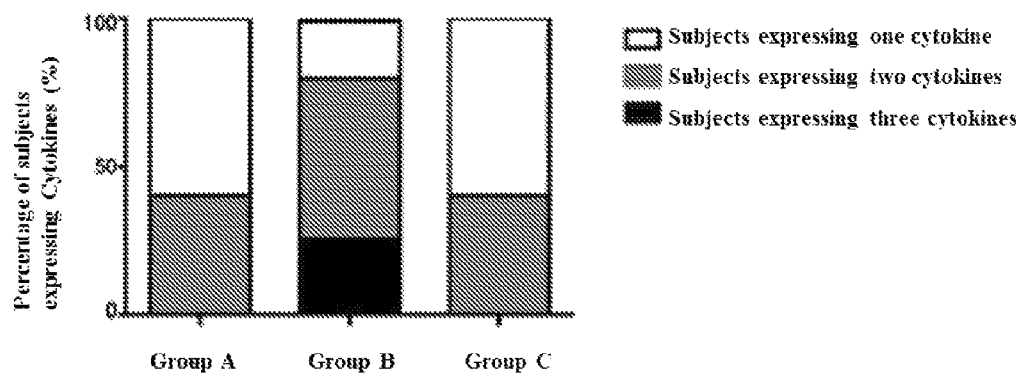
FIG. 7 illustrates PBMC cytokine production of vaccinated health human subjects under stimulation of one single peptide according to some embodiments of the present disclosure.

Furthermore, cytokine production of CD4+ T cells from one subject chosen according to results of ELISPOT is evaluated by flow cytometry. As illustrated in FIG. 7, under stimulation of one single peptide, CD4+ T cells from subjects in full-dosage group (Group B) express three cytokines (including IFN-γ, TNF-α, and IL-2), while CD4+ T cells from subjects in half-dosage group (Group B) and control group (Group C) express two of the three cytokines. FIG. 6 illustrates flow cytometry result of one subject in full-dosage group.

The results of the clinical studies indicate the full-dosage group and the half-dosage group show adequate tolerance to the composition. High-titer humoral immune responses and T cell mediated immune responses indicate the composition may elicit effective protection in chronic HBV subjects.

Example 6: Effects of the Composition on HBV Infected Patients

Patient One:

Mr. Zhao, male, 39 years old, has been infected with HBV (HBsAg+; HBeAg+; HBcAb+) for 9 years. He received anti-virus treatments by taking Lamivudine or Entecavir. After stopping taking anti-virus treatments for 2 months, a test showed that concentration of HBV-DNA was $3.6 \times 10^6$ copies/ml; concentration of HBsAg was greater than 225 ng/ml; concentration of HBeAg was greater than 76.5 PEIU/ml; anti-HBeAg antibody was negative; concentration of anti-HBcAg antibody was 3 PEIU/ml. The composition was administrated once every 2 weeks or 4 weeks. The composition including 40 μg HBsAg and 1000 μg PIKA was administrated each time. From day 112 after first administration to day 330 (final administration), dosage of the composition increased to 50 μg HBsAg and 1500 μg PIKA. From day 260, the concentration of the HBV-DNA started to decrease. On day 302, the concentration of the HBV-DNA was $1.5 \times 10^4$ copies/ml. Meanwhile, the concentration of HBeAg slowly decreased. After 2 years since first administration, the concentration of HBeAg reached 38.27 PEIU/ml. During administration of the composition, on day 42 concentration of ALT and AST showed a temporary raise, and from day 260 the concentration was back to normal.

Patient Two:

Mr. Song, male, 46 years old, has been infected with HBV (HBsAg+; HBeAb+; HBcAb+) for 4 years. He received anti-virus treatments by taking Anti-HBV TF. Before administration of the composition, a test showed that concentration of HBV-DNA was $6.0 \times 10^3$ copies/ml; concentration of HBsAg was greater than 225 ng/ml; HBeAg was negative; concentration of anti-HBeAg antibody was greater than 2.0 PEIU/ml; concentration of anti-HBcAg antibody was greater than 3.9 PEIU/ml; ALT was abnormal (57 U/L). The composition was administrated once every 2 weeks or 4 weeks. The composition including 40 µg HBsAg and 1000 µg PIKA was administrated each time. Starting from day 112 after first administration, dosage of the composition increased to 50 µg HBsAg and 1500 µg PIKA. On day 171, the concentration of the HBV-DNA decreased (<500 copies/nil). The concentration of HBsAg went down to 77.35 ng/ml, and ALT was back to normal. From day 246 to day 330, the composition including 60 µg HBsAg and 2000 µg PIKA was administrated once every two weeks or four weeks. After 2 years since first administration, the concentration of HBV-DNA was lower than 500 copies/ml, the concentration of HBsAg was 3.17 ng/ml, and the concentration of ALT went back to normal.

Patient Three:

Mr. Zhang, male, 32 years old, has been infected with HBV (HBsAg+; HBeAb+; HBcAb+) for 8 years. Before administration of the composition, a test showed that HBV-DNA was negative; concentration of HBsAg was greater than 225 ng/ml; HBeAg was negative; concentration of anti-HBeAg antibody was greater than 2.0 PEIU/ml; concentration of anti-HBcAg antibody was greater than 3.9 PEIU/ml. The composition was administrated once every 2 weeks or 4 weeks. The composition including 40 µg HBsAg and 1000 µg PIKA was administrated each time. Starting from day 112 after first administration, dosage of the composition increased to 50 µg HBsAg and 1500 µg PIKA. On day 171, the concentration of the HBsAg went down to 49.86 ng/ml.

Example 7. Effects of Different Types of the Composition

In EXAMPLE 7, 18 HBV-transgene mice which express high-level HBV DNA are used. All mice are divided into three groups (group A, group B, and group C), each of which includes 6 mice. According to Table 8, the compositions and other substances are administrated to each group of the mice. The compositions and other substances are administrated to the mice once a week for 12 weeks. A seven-day observation is performed after the final administration. The body weight of each mouse is measured twice a week. After the first administration, the HBV DNA is measured on day 0, day 21, and day 42, respectively.

TABLE 8

The compositions administrated to the mice

| Group name | PBS | The compositions | | |
|---|---|---|---|---|
| | | PIKA | HBsAg | HBcAg |
| group A | + | | | |
| group B | | 50 µg | 10 µg | |
| group C | | 50 µg | 10 µg | 10 µg |

Figure 8:
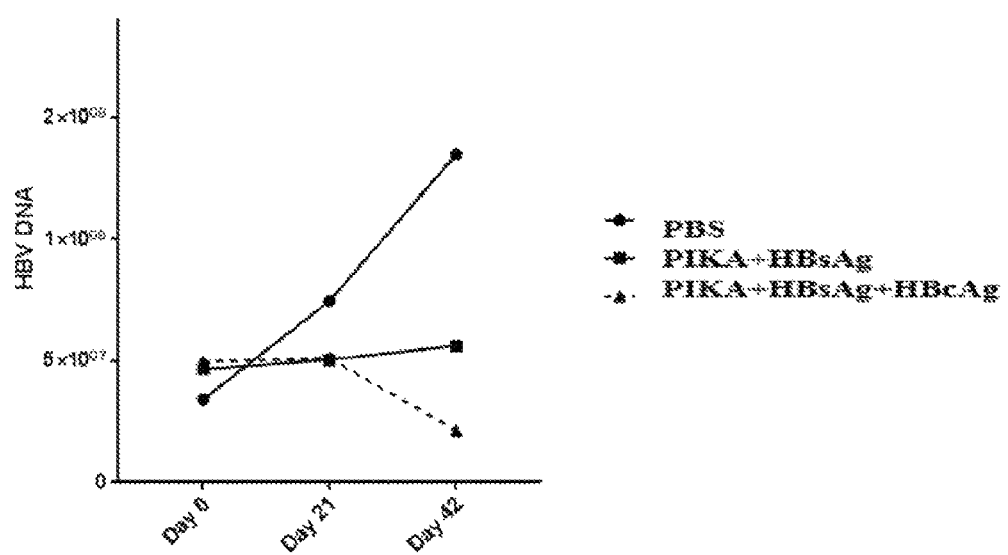
FIG. 8 illustrates effects of the composition on HBV-transgene mice according to some embodiments of the present disclosure.

According to FIG. 8, even in the mice expressing high-level HBV-DNA, after the compositions are administrated to the mice from the group B and group C, HBV DNA decreases, which indicates that the compositions significantly prevent and treat HBV infection.

It should be noted that the EXAMPLE 7 is merely by way of example. Those skilled in the art may change the form and details of the EXAMPLE 7 without departing the spirit and scope of the present disclosure. For example, ratio of the HBsAg and/or HBcAg to PIC (or PIKA) may be 1:50, 1:40, 1:30, 1:25, 1:20, 3:50, 1:15, 1:10, 1:5, or any value between 1:50 and 1:5.

Example 8. Stability of the Composition

In EXAMPLE 8, three batches of the composition are used. Each batch is divided into two groups (two groups are placed in an incubator adjusted to a temperature of 37° C., and 25° C., respectively). A hepatitis B vaccine which includes Alum adjuvant and HBsAg is used as control. The group of the composition placed at 37° C. for 1 week, 2 weeks, and 4 weeks is serially diluted and administrated to the mice. Blood samples are collected to measure HBsAb. Ratio of $ED_{50}$ of the composition and the control vaccine is measured. The group of the composition placed at 25° C. for 1 month, 2 months, 3 months and 4 months is serially diluted and administrated to the mice. Blood samples are collected to measure the HBsAb. Ratio of $ED_{50}$ of the composition and the control vaccine is measured.

According to Table 9, after placed at 37° C., the composition of the present disclosure shows higher potency than the control hepatitis B vaccine; after placed at 25° C., the composition of the present disclosure also shows higher potency and stability than the control hepatitis B vaccine.

TABLE 9

Stability study of the composition

| Potency | | Batch | | | | | |
|---|---|---|---|---|---|---|---|
| | | Alum + HBsAg | | | PIKA + HBsAg | | |
| Temperature | Time/duration | 1 | 2 | 3 | 1 | 2 | 3 |
| 4° C. | Day 0 | 6.2 | 6.2 | 4.4 | 8.2 | 7.4 | 11.7 |
| 37° C. | 1 week | 4.2 | 4.5 | 5.6 | 5.0 | 6.7 | 2.9 |
| | 2 weeks | 4.9 | 3.8 | 4.1 | 10.1 | 10.1 | 4.4 |
| | 4 weeks | 3.9 | 2.4 | 3.2 | 4.5 | 4.0 | 7.9 |
| 25° C. | 1 month | 6.3 | 5.6 | 5.4 | 10.9 | 24.2 | 7.9 |
| | 2 months | 5.4 | 5.4 | 5.7 | 13.1 | 9 | 7.4 |
| | 3 months | 3.0 | 4.4 | 3.9 | 14.1 | 17.9 | 7.1 |
| | 6 months | 1.7 | 2.3 | 1.8 | 18.3 | 9.3 | 9.9 |

It should be noted that although one type (i.e., composition including PIKA and HBsAg) of the composition is used in Example 8, the EXAMPLE 8 is illustrative and that the scope is not limited. To those skilled in the art, various changes in form and details of the EXAMPLE 8 may be made without departing from the scope of the present disclosure. Merely by way of example, another type (e.g., composition including PIKA, HBsAg and HBcAg) of the composition may be used in the EXAMPLE 8. For another example, those skilled in the art may use a different concentration of the composition, or a different concentration of each substance of the composition. For example, ratio of the HBsAg and/or HBcAg to PIC (or PIKA) may be 1:50, 1:40, 1:30, 1:25, 1:20, 3:50, 1:15, 1:10, 1:5, or any value between 1:50 and 1:5.

According to the present disclosure, the composition provides at least one of following advantages:
- good safety both in acute and chronic toxicological studies;
- enhancing humoral immune responses, and generating higher titer and earlier antibody production;
- effectively triggering T cell mediated immune responses;
- decreasing HBV DNA load in HBV infected subjects.

While the present disclosure has been described with reference to particular embodiments, it will be understood that the embodiments are illustrative and that the scope is not limited. Alternative embodiments of the present disclosure will become apparent to those having ordinary skill in the art to which the present disclosure pertains. Such alternate embodiments are considered to be encompassed within the spirit and scope of the present disclosure.

What is claimed is:

1. A composition comprising:
polyriboinosinic acid-polyribocytidylic acid (PIC), at least one antibiotic or polyamide compound, at least one positive ion, and HBsAg,
wherein the concentration of the HBsAg in the composition ranges from 20 μg/unit dose to 60 μg/unit dose.

2. The composition of claim 1, further comprising HBcAg.

3. The composition of claim 1, wherein the HBsAg is produced by *Hansenula polymorpha*, CHO cells, insect expression system, *Saccharomyces cerevisiae*, or *Pichia pastoris*.

4. The composition of claim 2, wherein the HBcAg is produced by *Escherichia coli, Hansenula polymorpha*, insect expression system, *Saccharomyces cerevisiae*, or *Pichia pastoris*.

5. The composition of claim 1, wherein the antibiotic is selected from a group including tobramycin, anthracycline, butyrosin sulfate, gentamicin, hygromycin, amikacin, dibekacin, nebramycin, beta-lactam, neomycin, puromycin, streptomycin, streptozotocin, and kanamycin.

6. The composition of claim 1, wherein the polyamide compound is selected from a group including spermidine salt, spermidine, N-(3-aminopropyl), N-(3-aminopropyl)-1,4-butandiamine, spermine BR, spermine, OS-dimethylphosphoramidothioate, polylysine, and aminoglycoside.

7. The composition of claim 1, wherein the positive ion is selected from a group including calcium, cadmium, lithium, magnesium, cerium, cesium, chromium, cobalt, deuterium, gallium, iodine, iron, and zinc.

8. The composition of claim 1, wherein ratio of the HBsAg to PIC is 1:30, 1:25, or 1:20.

9. The composition of claim 2, wherein ratio of the HBcAg to PIC is 1:30, 1:25, or 1:20.

10. The composition of claim 1, wherein concentration of PIC in the composition ranges from 250 μg/unit dose to 6000 μg/unit dose.

11. The composition of claim 1, wherein concentration of the PIC in the composition ranges from 500 μg/unit dose to 1500 μg/unit dose.

12. The composition of claim 2, wherein concentration of the HBcAg in the composition ranges from 10 μg/unit dose to 100 μg/unit dose.

13. The composition of claim 10, wherein one unit dose ranges from 0.1 ml to 250.0 ml.

14. The composition of claim 1, wherein the composition further comprises at least one substance selected from a group including gelatin, saccharose, granulated sugar, lactose, maltose, trehalose, glucose, low molecular dextran, sorbitol, polysorbate 20, mannitol PEG, human blood albumin, recombinant human serum albumin, sodium caprylate, urea, aluminum hydroxide, phenol red, magnesium chloride, potassium chloride, sodium chloride, sodium thiosulphate, potassium dihydrogen, ascorbic acid, trichloromethane, phenol, and thiomersal or at least one physiologically acceptable buffer, wherein the physiological acceptable buffer is selected from a group including acetate buffer, trisamine buffer, bicarbonate buffer, carbonate buffer, and phosphate buffered saline.

15. The composition of claim 1, wherein pH of said composition ranges from 6.0 to 8.0.

16. The composition of claim 1, wherein the composition is in a liquid or solid form, wherein said liquid form is selected from a group including parenteral solution, suspension, ointment, emulsion, drop, syrup, and gel; wherein said solid form is selected from a group including dry powder, freeze-dried powder, tablet, capsule, suppository, granule, and sugar-coated tablet.

17. A method for treating and/or prevention Hepatitis B virus infection, comprising administering a composition to a subject, wherein said composition comprises PIC, at least one antibiotic or polyamide compound, at least one positive ion, and HBsAg,
wherein the concentration of the HBsAg in the composition ranges from 20 μg/unit dose to 60 μg/unit dose.

18. The method of claim 17, said method further comprising administering the composition to the subject once every two months, twice every two months, three times every two months, four times every two months, five times every two months, once every month, twice every month, once every three weeks, twice every three weeks, twice every two weeks, once every two weeks, or once every week or wherein the composition is administered to the subject by one way selected from a group including intramuscular injection, intraperitoneal injection, intravenous injection, subcutaneous injection, transdermal delivery, intradermal delivery, nasal delivery, opthamalical delivery, oral delivery, sublingual delivery, peritumoral delivery, and intratumor delivery.

19. The method of claim 17, wherein said subject is a HBV uninfected subject, a chronic HBV subject, or an acute HBV subject.

20. The method of claim 17, wherein the concentration of the HBsAg in the composition ranges from 40 μg/unit dose to 60 μg/unit dose and the concentration of the PIC in the composition ranges from 1000 μg/unit dose to 1500 μg/unit dose.

21. The composition of claim 1, wherein the composition comprises an antibiotic, wherein the antibiotic comprises kanamycin and the positive ion comprises calcium.

* * * * *